United States Patent [19]
Kuhner

[11] Patent Number: 5,131,282
[45] Date of Patent: Jul. 21, 1992

[54] MINIMUM EMISSION CLOSED LOOP SAMPLING SYSTEM FOR TRANSPORTABLE CONTAINERS

[75] Inventor: S. Wayne Kuhner, Worthington, Ky.

[73] Assignee: Ashland Oil, Inc., Ashland, Ky.

[21] Appl. No.: 631,828

[22] Filed: Dec. 21, 1990

[51] Int. Cl.⁵ .............................................. G01N 1/10
[52] U.S. Cl. ................................................ 73/863.71
[58] Field of Search ............... 73/863.61, 863.71, 863.81–863.86, 73/864.73, 864.51, 864.63, 864.91

[56] References Cited
U.S. PATENT DOCUMENTS

| | | | |
|---|---|---|---|
| 258,872 | 6/1882 | Ashcroft | 340/624 |
| 4,628,749 | 12/1986 | Rafter, Jr. | 73/863.71 |
| 4,712,434 | 12/1987 | Herwig et al. | 73/863.71 |
| 4,987,785 | 1/1991 | Spencer | 73/863.71 |

Primary Examiner—Robert Raevis
Attorney, Agent, or Firm—Richard C. Willson, Jr.; Stanley M. Welsh

[57] ABSTRACT

Closed loop sampling system using quick-connects dramatically reduces emission of sampled hydrocarbons and other fluids to the atmosphere.

6 Claims, 5 Drawing Sheets

MINIMUM EMISSION CLOSED LOOP SAMPLING SYSTEM FOR TRANSPORTABLE CONTAINERS

BACKGROUND OF THE INVENTION

I. Field of the Invention

The present invention relates to methods of sampling of fluids, both gases and liquids, generally classified in U.S. Patent Office Class 73, particularly subclasses 863, and most especially subclasses 863.41, 863.71, 863.72, 863.73, 863.81, 863.82, and 863.85

II. Description of the Prior Art

With refinements in analytical techniques, the need for more sophisticated methods of sampling has become evident to industry. Also, emphasis on environmental consideration has reduced the tolerable amounts of sampling effluents which are acceptable. A number of prior patents have dealt with solutions to prior patents of combining a representative sample with minimum pollution.

U.S. Pat. No. 4,712,434 to Herwig (assigned E C Erdolchemie GmbH) uses a special single four-way valve and a complex flushing mechanism to provide a flow through sample in a transportable container.

U.S. Pat. No. 4,800,763 to Kakkers (assigned VEG-Gasinstituut) teaches periodic sampling from a pipeline, but uses no transportable container.

U.S. Pat. No. 4,800,761 to Spencer provides a flow through sample in a transportable container, but uses a special drill block which incorporates a venturi together with a three-way valve for alternately flushing and filling the container.

U.S. Pat. No. 4,755,357 to Noguchi (assigned Horiba, Ltd) uses a four-way valve or several three-way valves, but requires two parallel capillaries as in a gas-liquid chromatograph and provides no transportable container sample.

U.S. Pat. No. 4,827,775 to Forrester also provides no transportable sample container and performs its sampling within a closed manway with the sample being delivered to a permanently connected pipeline.

U.S. Pat. No. 3,681,997 to Allen (assigned Gulf Refining) is also a pipeline sampler with no transportable container being provided.

U.S. Pat. No. 3,960,500 to Ross (assigned Bailey Meter Co.) utilizes a drop tube device to obtain a representative sample, but provides no transportable sample container.

U.S. Pat. No. 4,167,117 to Stokley (assigned Exxon Production Research Co.) utilizes a pitot-like tube to obtain a representative sample flowing through a pipeline, e.g. sand and crude oil from a well and provides no transportable sample container.

While each of the above prior art are valuable for their intended purposes, none of the references provides, in combination, a flow through sample, a transportable sample container, and the extremely low venting of the sample material which is achieved by the present invention.

SUMMARY OF THE INVENTION

I. General Statement of the Invention

The present invention combines a transportable container means which is attached by quick-connect means to a sampling system which provides alternately flushing and flow through the sample container. The quick-connect means of the invention are low volume, self closing valves which provide minimal contamination to the atmosphere and can be connected and disconnected quickly with one hand and without requiring any tools.

II. Utility of the Invention

The present invention is useful for providing representative samples of a wide variety of fluids including hydrocarbons, especially gasoline, diesel fuel, propane, butane, hydrogen, and more hazardous materials, e.g. hydrogen sulfide, and other toxic and/or corrosive materials.

DESCRIPTION OF THE PREFERRED EMBODIMENTS

Figure 1:
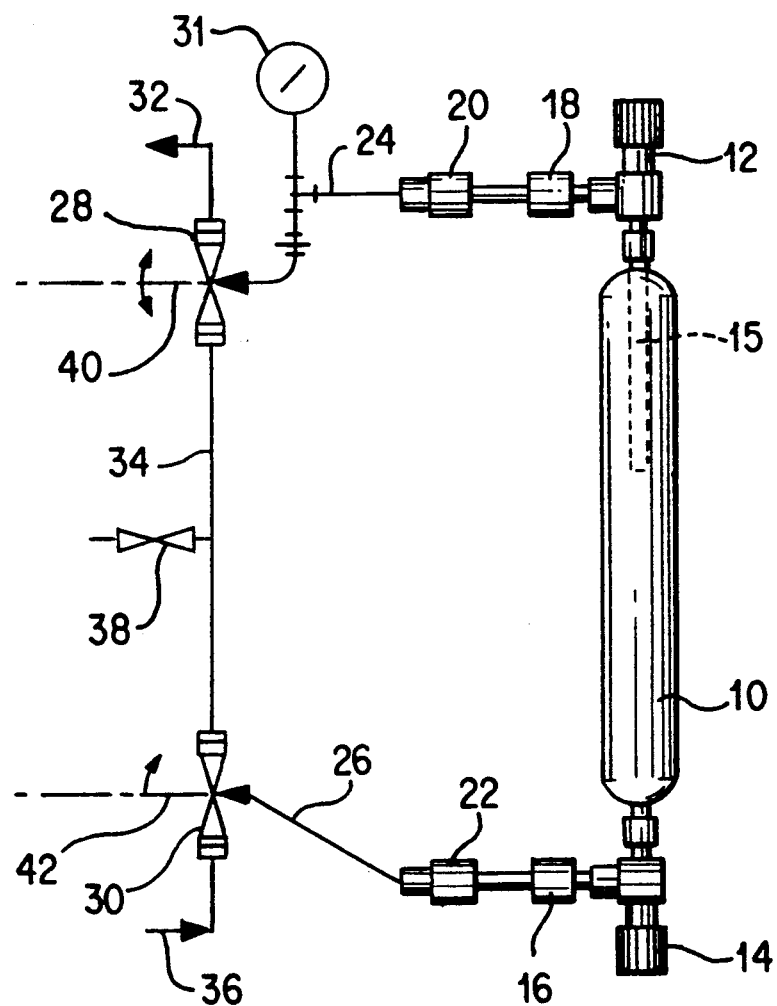
FIG. 1 is a schematic diagram of a preferred embodiment of the present invention.

Referring to FIG. 1, sample container 10 is a conventional stainless steel pressure cylinder fitted with right-angle shut-off valves and equipped with a outage tube extending down into the container for at least 20% of the container's interior length, more preferably for 25-60%, and most preferably about 30% of its length. (This outage tube 15 prevents over-filling of the cylinder of liquid which could expand causing rupture of the cylinder, and also prevents sediment collected with some samples from being expelled into the delicate analytical instruments.) Cylinder 10 can be made of stainless steel, monel, or any other strong material suitable chemically to resist corrosion by the sample to be taken, and sufficiently strong physically to contain any vapor pressure or compressed gas pressure exerted by the sample. Sample container preferably has no rupture disc, spring loaded safety valve, or other safety valve, any of which could either be punctured by corrosion or provide a difficult to detect site of leakage which might change the composition of the sample. Valve 12 is connected to the male portion of a commercial quick-connect self-closing valve, e.g. the Series "QC" manufactured by Swagelok, Inc. Lower valve 14 is similarly equipped with a male quick-connect self-closing valve 16. Together these male self-closing valves and the elements between them comprise a transportable sampling device which can be used to sample gases or liquids at a remote location, e.g. a refinery or oil production field, and then transported to a central quality control or other analytical facility.

The non-transportable sample-providing piping system begins with a female connector 20 which is mateable with male connector 18 and a corresponding female connector 22 which mates with lower male connector 16.

Female connector 20 is permanently attached to conduit 24 which is shown schematically as having some length, but which is preferably connected essentially flush with the three-way valve. Similarly, female self-closing quick-connect valve 22 is also connected flush or as close as possible to its respective three-way valve.

Three-way valve 28 is preferably a ball valve, but can be a plug valve or other type if desirable due to the particular circumstances and fluids being handled. A preferred three-way valve is the Series 40 manufactured by Whitey Corp. Three-way valve 28 is connected to female quick-connect 20 as described above, and also to conduit 32, the return line to the process from which the sample is being taken, e.g. refinery processing unit or production well, and three-way valve 28 is also connected to by-pass line 34, which connects to the lower three-way valve 30, which in turn connects to sample inlet line 36. Optional vent means 38 can be provided in by-pass line 34 and can be connected to a flare, neutralizing pit, or other disposal unit, suitable for the material being sampled. Three-way valves 28 and 30 are controlled by handles 40 and 42, respectively. Handles 40 and 42 can be swung upward and downward to connect alternately for sample mode and vent mode.

Figure 2:
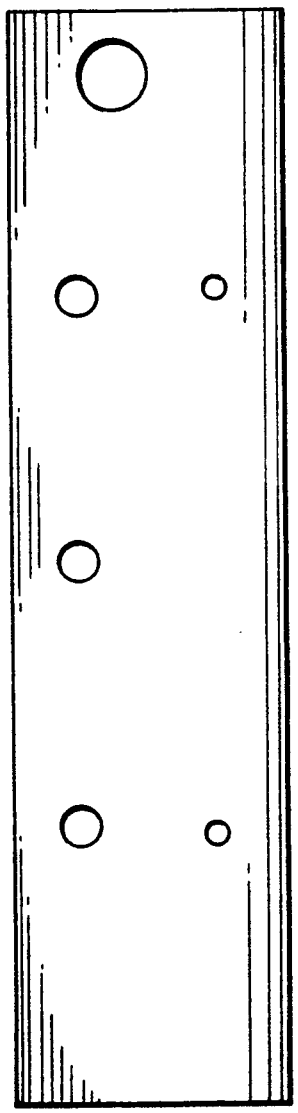
FIG. 2 is a front view of a convenient panel for mounting the present invention so that the sample container with its quick-connects can be "bayonetted" into the sample source piping.
Figure 3:
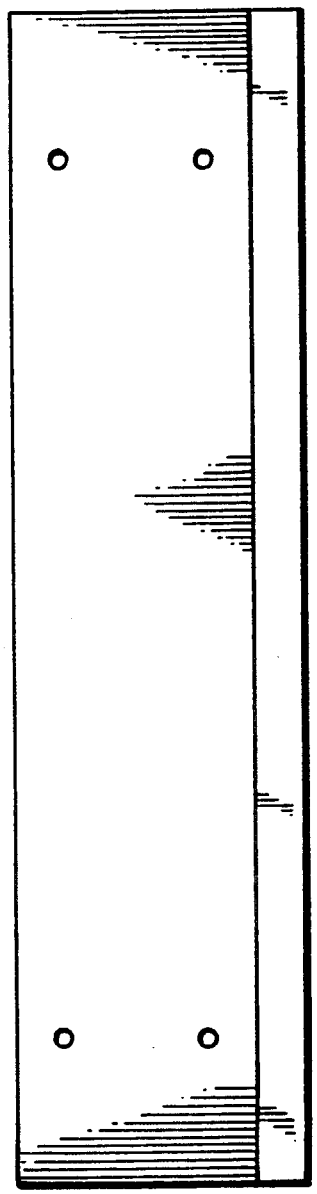
FIG. 3 is a left side view of the mounting bracket of FIG. 2.
Figure 4:
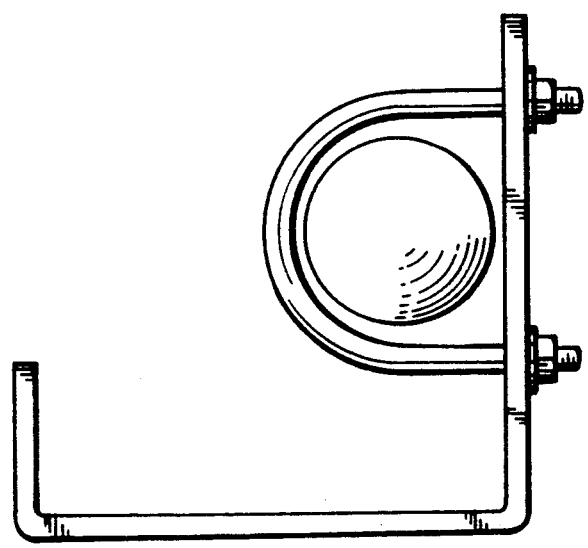
FIG. 4 is a plan view of the mounting bracket of FIG. 2.
Figure 5:
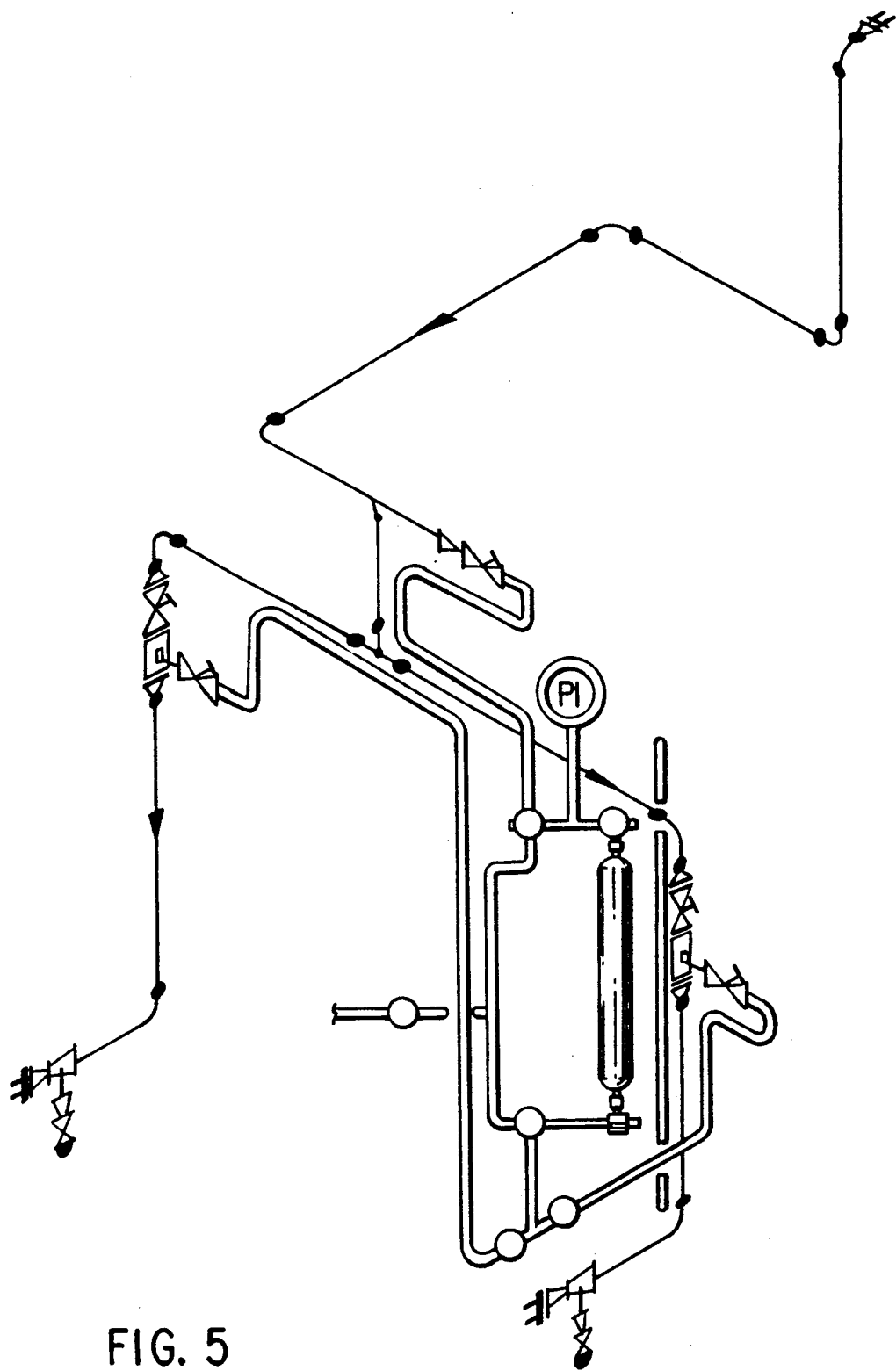
FIG. 5 is a schematic isometric view of a typical installation of the apparatus of FIG. 1 in typical process piping.

In operation, sample container 10 with its attached male quick-connects 18 and 16, and with its inlet and outlet valves 12 and 14 in the open position, is "stabed" or "bayonnetted" into the female quick-connects 20 and 22 which are held in exact alignment by means of the piping and the brackets as shown in FIGS. 2-4. This is a simple operation even under adverse circumstances, facilitating the collection of samples.

Valves 40 and 42 are shown with the handles in the normal shut-off position with the handle extending horizontally. Once the sample container 10 has been connected, after checking pressure gauge 31 shows near atmospheric pressure, handle 40 is swung upward to the vertical position so that the sample bomb is connected with the sample return line 32. Then handle 42 is swung downward to the vertical position so that the sample container is connected to the sample inlet line 36. Flow now proceeds through the sample container 10, flushing the container and assuring a representative sample. After a few seconds or a few minutes (depending on the flow rate and the fluid to be sampled), the handle 40 is returned to the horizontal or off position as shown in FIG. 1. Similarly, handle 42 is swung to the horizontal or off position as shown in FIG. 1. This shuts off flow and isolates the sample in the sample container.

Next, right-angle valve 12 is closed, sealing the upper outlet of the sample container 10. Then, lower right-angle valve 14 is closed, sealing the sample into the sample container 10.

Next, the sample system is vented by opening vent valve 38, a common two-way valve of suitable materials which may be ball, plug, gate, or other suitable design. Valve handle 40 is swung to the lower vertical position connecting by-pass line 34 with female quick-connect 20.

Next, handle 42 is swung to the vertical up position so that quick-connect 22 is connected to by-pass line 34, completing the venting process through valve 38.

Lastly, handles 40 and 42 are both returned to the horizontal (off) position and vent valve 38 is closed, completing the sampling procedure. The sampling cylinder is pulled to release male quick-connects 18 and 16 from their female counterparts 20 and 22, and the sampling cylinder is transported to the analysis point. Venting during disconnect amounts to less than about 0.1 cubic centimeter for both valves. This amount of venting is tolerable even for highly hazardous substances.

MODIFICATIONS

Specific compositions, methods, or embodiments discussed are intended to be only illustrative of the invention disclosed by this specification. Variation on these compositions, methods, or embodiments are readily apparent to a person of skill in the art based upon the teachings of this specification and are therefore intended to be included as part of the inventions disclosed herein. For example, though the quick connects 20 and 22 are shown as in the same plane, they could be at right angles to each other and the mating quick connects 16 and 18 similarly arranged at right angles, so one set may be stabbed together and the others swung together by pivoting on the first set.

Reference to documents made in the specification is intended to result in such patents or literature being expressly incorporated herein by reference including any patents or other literature references cited within such documents.

What is claimed is:

1. A sampling system for sampling fluids with minimal hand operations and with minimum atmospheric contamination, said system comprising in combination:
    A. transportable container means for containing samples having provision for flowing liquids through said container means, and comprising an inlet valve and an outlet valve mounted on substantially opposite portions of said container means;
    B. self-closing quick connect valve means connected to said inlet valve and said outlet valve;
    C. two three-position valves having quick-connect means to mate with said quick-connect means mounted on said inlet and said outlet valve, said three-position valves being alternately configured to a sample mode in which a liquid sample flows through said container means, a venting mode in which conduits leading to said container means from the source of said fluid to be sampled are vented to suitable disposal means for receiving vented fluid, and a shut-off mode in which flow is blocked through said three-way valves, wherein said container means is equipped with an outage tube.

2. A system according to claim 1, wherein the container means comprises an outage tube extending into said container and connecting with a fill valve mounted on said container.

3. A system according to claim 1, wherein said quick-connect means are self-closing and have low interior volume.

4. A system according to claim 1, wherein said inlet valve and said outlet valve are right-angle valves the outlets of which face in the same direction.

5. A system according to claim 1, wherein said quick-connect means mounted in communication with said three-way valves are spaced apart and are arranged geometrically so as to simultaneously engage the respective quick-connect means on said transportable container means.

6. A system according to claim 1, wherein said quick connect means communicating with said three-way valves are mounted on a panel and wherein the handles of said three-way valves extend through another position on said panel, whereby said quick-connects on said inlet and said outlet valve of said transportable container means can be simultaneously bayoneted into said quick-connects on said panel.

* * * * *